(12) United States Patent
Govari et al.

(10) Patent No.: US 11,911,096 B2
(45) Date of Patent: Feb. 27, 2024

(54) DETECTING CONTACT AND PROXIMITY BETWEEN ABLATION ELECTRODES BY SENSING CHANGES IN VOLTAGE MORPHOLOGY OF NON-ACTIVATED ELECTRODES

(71) Applicant: BIOSENSE WEBSTER (ISRAEL) LTD., Yokneam (IL)

(72) Inventors: Assaf Govari, Haifa (IL); Andres Claudio Altmann, Haifa (IL); Lilah Marziano, Ganey-Tikva (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 193 days.

(21) Appl. No.: 17/124,943

(22) Filed: Dec. 17, 2020

(65) Prior Publication Data

US 2022/0192736 A1 Jun. 23, 2022

(51) Int. Cl.
*A61B 18/14* (2006.01)
*A61B 34/20* (2016.01)
(Continued)

(52) U.S. Cl.
CPC ............ *A61B 18/1492* (2013.01); *A61B 2018/00351* (2013.01); *A61B 2018/00363* (2013.01);
(Continued)

(58) Field of Classification Search
CPC ............ A61B 18/1492; A61B 18/1206; A61B 2018/00892; A61B 2018/00577;
(Continued)

(56) References Cited

U.S. PATENT DOCUMENTS 8,048,067 B2 11/2011 Davalos
8,221,411 B2 7/2012 Francischelli
(Continued)

FOREIGN PATENT DOCUMENTS

CN 106456972 A 2/2017
DE 102007018841 A1 10/2008
(Continued)

OTHER PUBLICATIONS

European Search Report for corresponding EPA No. 21165819.0 dated Sep. 21, 2021.

*Primary Examiner* — Aaron F Roane

(57) ABSTRACT

A system includes a catheter, a pulse generator and a controller. The catheter is configured for insertion into a body of a patient, and includes at least a first electrode, a second electrode and a third electrode, which are disposed at a distal end of the catheter and are configured to contact tissue within the body. The pulse generator is configured to apply one or more bipolar ablation pulses between the first and second electrodes, for ablating the tissue in contact with the first and second electrodes. The controller is configured to: (i) control the pulse generator to apply the one or more bipolar ablation pulses between the first and second electrodes, (ii) receive a signal indicative of a voltage, measured between the third electrode and a reference during application of the ablation pulses, and (iii) issue a notification in response to detecting that the voltage violates a predefined criterion.

12 Claims, 3 Drawing Sheets

(51) Int. Cl.
    *A61B 18/00* (2006.01)
    *A61B 18/12* (2006.01)
(52) U.S. Cl.
    CPC ............... *A61B 2018/00375* (2013.01); *A61B 2018/00577* (2013.01); *A61B 2018/00613* (2013.01); *A61B 2018/00892* (2013.01); *A61B 2018/126* (2013.01); *A61B 2018/1467* (2013.01); *A61B 2034/2051* (2016.02)
(58) Field of Classification Search
    CPC .. A61B 2018/00898; A61B 2018/1467; A61B 18/1233; A61B 2018/126
    See application file for complete search history.

(56) References Cited

U.S. PATENT DOCUMENTS

| | | | |
|---|---|---|---|
| 9,297,845 | B2 | 3/2016 | Mathur |
| 9,561,377 | B2 | 2/2017 | Gunderson |
| 10,271,893 | B2 | 4/2019 | Stewart |
| 10,342,598 | B2 | 7/2019 | Long |
| 10,531,914 | B2 | 1/2020 | Stewart |
| 10,820,800 | B2 | 11/2020 | Ruppersberg |
| 2006/0009754 | A1 | 1/2006 | Boese |
| 2008/0281322 | A1* | 11/2008 | Sherman ............ A61B 18/1206 606/42 |
| 2009/0036885 | A1* | 2/2009 | Gregg ................ A61B 18/1233 606/35 |
| 2011/0245888 | A1 | 10/2011 | Badelt |
| 2013/0289551 | A1 | 10/2013 | Condie |
| 2014/0276765 | A1* | 9/2014 | Blix .................... A61B 18/1206 606/34 |
| 2014/0276769 | A1 | 9/2014 | Goertzen |
| 2015/0272655 | A1* | 10/2015 | Condie ............... A61B 18/1233 606/34 |
| 2015/0374427 | A1* | 12/2015 | Goertzen ............... A61B 34/20 606/34 |
| 2016/0051324 | A1 | 2/2016 | Stewart |
| 2018/0001085 | A1 | 1/2018 | Cadossi |
| 2019/0038349 | A1* | 2/2019 | Koblish ............. A61B 18/1206 |
| 2019/0307500 | A1 | 10/2019 | Byrd |
| 2020/0015876 | A1 | 1/2020 | Chou |
| 2020/0229866 | A1 | 7/2020 | Harlev |

FOREIGN PATENT DOCUMENTS

| | | |
|---|---|---|
| JP | 03857354 B2 | 12/2006 |
| RU | 2413551 C2 | 3/2011 |
| WO | WO2007086965 A2 | 8/2007 |

\* cited by examiner

DETECTING CONTACT AND PROXIMITY BETWEEN ABLATION ELECTRODES BY SENSING CHANGES IN VOLTAGE MORPHOLOGY OF NON-ACTIVATED ELECTRODES

FIELD OF THE INVENTION

The present invention relates generally to medical devices, and particularly to methods and systems for improving bipolar ablations using flexible catheters.

BACKGROUND OF THE INVENTION

Various techniques for controlling bipolar ablation procedures and electroporation procedures have been published.

For example, U.S. Patent Application Publication 2019/0307500 describes electroporation systems, methods of controlling electroporation systems to limit electroporation arcs through intra-cardiac catheters, and catheters for electroporation systems. One method of controlling an electroporation system including a direct current (DC) energy source, a return electrode connected to the DC energy source, and a catheter connected to the DC energy source is disclosed. The catheter has at least one catheter electrode. The method includes positioning the return electrode near a target location within a body and positioning the catheter electrode adjacent the target location within the body. A system impedance is determined with the return electrode positioned near the target location and the catheter electrode positioned within the body. The system impedance is adjusted to a target impedance to arcing from the catheter electrode.

U.S. Patent Application Publication 2014/0276769 describes a medical device system configured to detect an improper energy transmission configuration therein. The condition may be detected by way of a detection of a condition where an energy-transmitting electrode of the medical device system becomes too close to or becomes in contact with an object resulting in an inability of the electrode to properly transmit energy. For example, if the energy-transmitting electrode is a first electrode configured in its operational state to transmit energy to bodily tissue adjacent the first electrode, but the first electrode is inadvertently contacting a second electrode, such contact may cause at least some energy transmitted by the first electrode to follow an unintended path away from its intended path to the adjacent tissue. Such a condition may be detected based at least upon an analysis of information acquired from a sensing device system.

SUMMARY OF THE INVENTION

An embodiment of the present invention that is described herein provides a system including a catheter, a pulse generator and a controller. The catheter is configured for insertion into a body of a patient, the catheter including at least a first electrode, a second electrode and a third electrode, which are disposed at a distal end of the catheter and are configured to contact tissue within the body. The pulse generator is configured to apply one or more bipolar ablation pulses between the first and second electrodes, for ablating the tissue in contact with the first and second electrodes. The controller is configured to: (i) control the pulse generator to apply the one or more bipolar ablation pulses between the first and second electrodes, (ii) receive a signal indicative of a voltage, measured between the third electrode and a reference during application of the ablation pulses, and (iii) issue a notification in response to detecting that the voltage violates a predefined criterion.

In some embodiments, in detecting that the voltage violates the predefined criterion, the controller is configured to detect that a distance between (i) at least one of the first and second electrodes, and (ii) the third electrodes, is smaller than a distance threshold. In other embodiments, the pulse generator includes first, second and third pulse-generation circuits having respective output transformers, which are connected between the reference and the first, second and third electrodes, respectively, and are configured to apply the bipolar ablation pulses to the first, second and third electrodes, respectively. In yet other embodiments, for measurement of the signal indicative of the voltage between the third electrode and the reference, the controller is configured to disconnect the third electrode from the third output transformer.

There is additionally provided, in accordance with an embodiment of the present invention, a method that includes inserting into a body of a patient, a catheter including at least a first electrode, a second electrode and a third electrode, which are disposed at a distal end of the catheter for making contact with tissue within the body. One or more bipolar ablation pulses are applied between the first and second electrodes, for ablating the tissue in contact with the first and second electrodes. A signal, which is indicative of a voltage measured between the third electrode and a reference during application of the ablation pulses, is received. A notification is issued in response to detecting that the voltage violates a predefined criterion.

BRIEF DESCRIPTION OF THE DRAWINGS

The present invention will be more fully understood from the following detailed description of the embodiments thereof, taken together with the drawings in which.

DETAILED DESCRIPTION OF EMBODIMENTS

Overview

Figure 1:
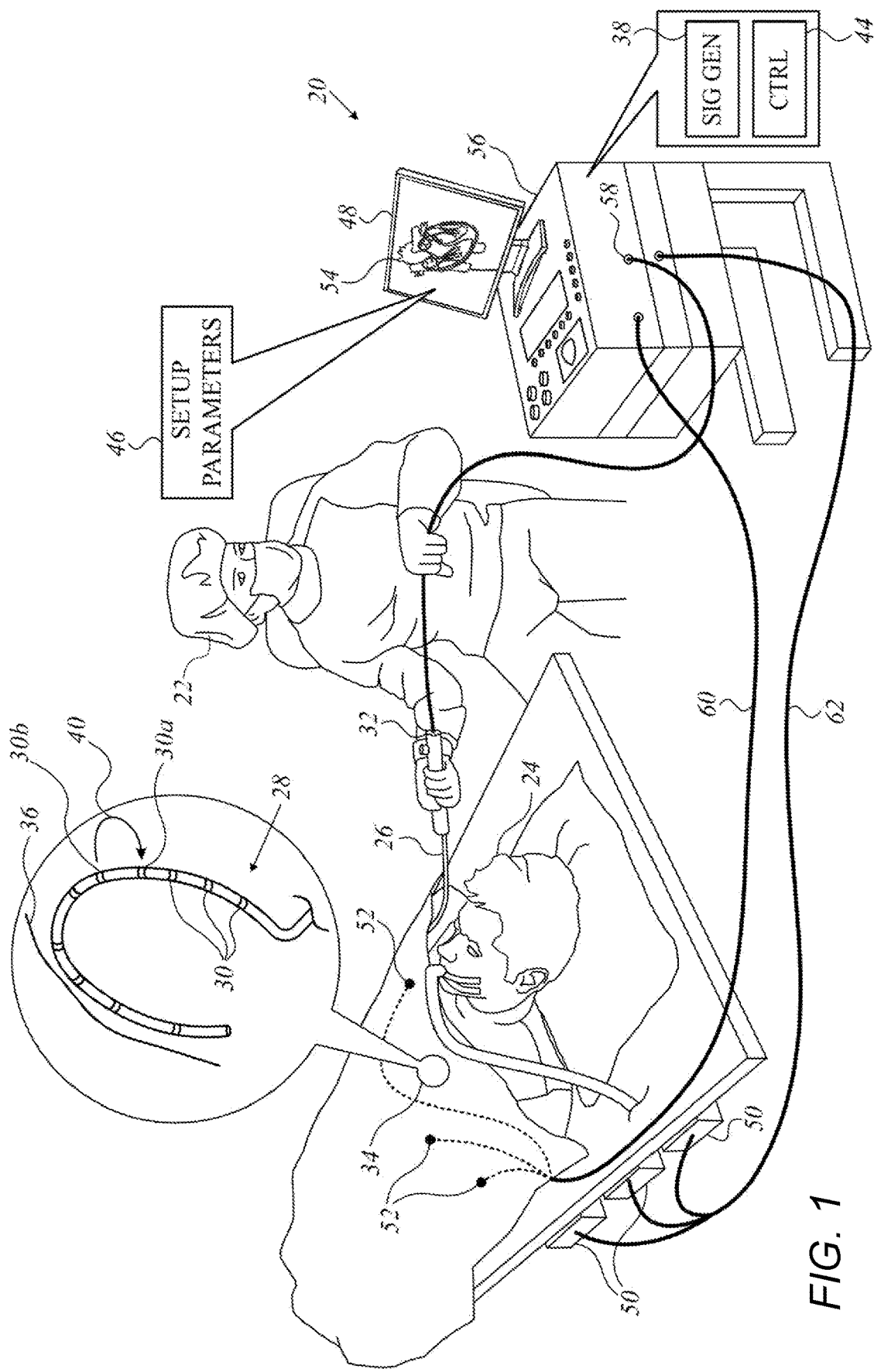
FIG. 1 is a schematic pictorial illustration of an ablation system in the course of a cardiac ablation procedure, in accordance with an exemplary embodiment of the invention.

Procedures for ablating soft tissue, such as irreversible electroporation (IRE) and radio frequency ablation (RFA) procedures, may comprise applying bipolar ablation pulses, e.g., between two ablation electrodes of a catheter, which is inserted into a patient organ for ablating the tissue in question.

In principle, it is possible to use a flexible catheter, which conforms to the tissue intended to be ablated. In some cases, however, the catheter flexibility may enable undesired proximity or even physical contact between two or more electrodes of the catheter. Such proximity or contact may divert at least part of the ablation energy, for example, to undesired locations on tissue of a patient, and may also cause inadequate ablation of the tissue intended to be ablated.

Embodiments of the present invention that are described hereinbelow provide improved techniques for controlling IRE and bipolar RFA procedures while retaining a safe distance between ablation electrodes of one or more ablation catheters inserted into the patient organ to carry out the tissue ablation.

In some embodiments, a system for ablating tissue comprises a catheter, a pulse generator and a controller. The catheter is configured for insertion into a body of a patient, and comprising at least a first electrode, a second electrode and a third electrode, which are disposed at a distal end of the catheter and are configured to be placed in contact tissue intended to be ablated.

In some embodiments, the pulse generator is configured to apply one or more bipolar ablation pulses between the first and second electrodes, also referred to herein as active electrodes, for ablating the tissue in contact with the first and second electrodes.

In some embodiments, the controller is configured to control the pulse generator to apply the one or more bipolar ablation pulses between the active electrodes. The controller is further configured to receive a signal indicative of a voltage, measured between the third electrode and a reference when applying the ablation pulses to the active electrodes. Note that the aforementioned ablation pulses are not applied to the third electrode, and therefore, in the present configuration, the third electrode is also referred to herein as a non-active electrode.

In some embodiments, the controller is configured to issue a notification in response to detecting that the voltage violates a predefined criterion.

Additionally or alternatively, based on the sensed voltage described above, the controller is configured to estimate the distance between given active and non-active electrodes, and to issue a notification in case the estimated distance is smaller than a distance threshold indicative of the minimal distance allowed between the given electrodes.

Based on the disclosed techniques, the controller is configured to sense and notify the user of the ablation system when at least a portion of the energy of the ablation pulses is diverted from the active electrode to the non-active electrode. Thus, the disclosed techniques improve the quality of bipolar ablation procedures, and enable the use of flexible catheter while improving the patient safety in IRE and bipolar RFA procedures.

System Description

FIG. 1 is a schematic pictorial illustration of an ablation system 20 in the course of a cardiac ablation procedure, in accordance with an embodiment of the invention. In some embodiments, a physician 22 performs the ablation procedure on tissue 36 of a patient 24, using an ablation catheter 26 whose distal end 28 is flexible, so as to conform with tissue 36, and comprises multiple ablation electrodes 30. The ablation procedure may comprise either an irreversible electroporation (IRE) procedure or a bipolar radiofrequency ablation (RFA) procedure, or possibly a combination of both kinds of ablation procedures.

In some embodiment, physician 22 is performing the cardiac ablation procedure using ablation system 20. To begin the procedure, physician 22 inserts catheter 26 into the body of patient 24, and then navigates the catheter, using a control handle 32, to a target site within, or external to, a heart 34 of patient 24. Subsequently, physician 22 places distal end 28 in contact with tissue 36 of heart 34, such as myocardial or epicardial tissue.

In some embodiment, physician 22 selects from among electrodes 30, a pair of electrodes 30a and 30b to carry out the bipolar ablation. System 20 comprises a pulse generator, also referred to herein as an electrical signal generator (SIG GEN) 38, or a generator 38 for brevity. Physician 22 controls generator 38 to generate ablation pulses 40, with signal parameters selected, for example, to serve as either IRE signals or RFA signals, or any suitable combination thereof.

In some embodiments, signals 40 are carried through catheter 26, over different respective channels, to ablation electrodes 30a and 30b, such that the ablation current flows from one of the electrodes in the pair through tissue 36 of patient 24, and returns through the other electrode of the pair.

In some embodiments, ablation system 20 further comprises a controller (CTRL) 44, which is configured to receive, from physician 22 or from another user, prior to and/or during the ablation procedure, setup parameters 46 suitable for the procedure. For example, using one or more suitable input devices, such as a keyboard, mouse, or touch screen, physician 22 defines the ablation mode (IRE, RFA), the parameters of the ablation pulses (for example power, duration), and one or more pairs of ablation electrodes 30 to be used for the ablation.

In some embodiments, physician 22 may also input, using the aforementioned input devices, additional setup parameters 46 for ablation pulse 40, such as but not limited to a maximum power, a maximum current amplitude, a maximum voltage amplitude, duration of the signal, and/or any other relevant parameters. In response to receiving setup parameters 46, controller 44 is configured to control signal generator 38, to generate signals 40 in accordance with the setup parameters. Moreover, controller 44 is configured to display the setup parameters on a display 48, which may comprise the aforementioned touch screen.

In some embodiments, controller 44 is configured to track the respective positions of ablation electrodes 30 in the patient's body during the procedure, using any suitable tracking technique. For example, distal end 28 may comprise at least a magnetic position sensor (not shown), which is configured, in the presence of external magnetic fields generated by magnetic field-generators 50, to output position signals indicative the positions of the respective sensor.

In some embodiments, based on the position signals, controller 44 is configured to estimate the positions of distal end 28 and electrodes 30. In alternative embodiments, for each electrode, controller 44 may receive multiple signals indicative of respective impedances measured between each electrode and multiple external electrodes 52 disposed on the body surface of patient 24 at various different locations. In some embodiments, controller 44 is configured to compute the ratios between the received impedances so as to estimate the position of the respective electrode within the body of patient 24. As yet another alternative, the controller 44 may use both magnetic-based tracking and impedance-based tracking, as described, for example, in U.S. Pat. No. 8,456,182, whose disclosure is incorporated herein by reference.

In some embodiments, distal end 28 may have additional sensors, such as but not limited to contact force sensors, configured to produce contact signals indicative of the contact between an electrode 30 and tissue 36. Based on the position signals and contact signal, controller 44 is configured to display which ablation electrodes 30 are in contact with tissue 36. In the present example, electrodes 30a and 30b are in contact with tissue 36, and in response to instructions from physician 22, controller 44 is configured to control signal generator 38 to apply ablation pulses 40 to tissue 36 via electrodes 30a and 30b. Note that other electrodes 30 of distal end 28 are not receiving ablation pulses 40, and are referred to herein as "non-activated electrodes," whereas in the present example, electrodes 30a and 30b are also referred to herein as "activated electrodes."

In some embodiments, controller 44 displays, on display 48, an image 54 of the patient's anatomy, with the position and orientation of distal end 28 overlaid on image 54. Additionally or alternatively, based on signals received from additional sensors disposed on distal end 28, controller 44 is configured to track the temperature and/or impedance of tissue 36, and to control signal generator 38 responsively thereto.

In some embodiments, ablation system 20 comprises a control console 56 having controller 44, signal generator 38 and display 48. Catheter 26 is electrically connected to console 56 via an electrical interface 58, such as a port or socket. Signals 40 are thus carried to distal end 28 via interface 58. Similarly, signals for tracking the position of distal end 28 and/or signals for tracking the temperature and/or impedance sensed in tissue 36 may be received by controller 44 via interface 58. Magnetic field-generators 50 and external electrodes 52 are connected to console 56 via cables 60 and 62, respectively.

In some embodiments, controller 44 typically comprises both analog and digital elements. Thus, controller 44 may comprise multiple analog-to-digital converters (ADCs) for receiving analog signals from catheter 26 and from signal generator 38. Controller 44 may further comprise multiple digital-to-analog converters (DACs) for transmitting analog control signals to signal generator 38 and other system components. Alternatively, these control signals may be transmitted in digital form, provided that signal generator 38 is configured to receive digital control signals. Controller 44 typically comprises digital filters for extracting signals at given frequencies from the received signals.

Typically, the functionality of controller 44, as described herein, is implemented at least partly in software. For example, controller 44 may comprise a programmed digital computing device comprising at least a central processing unit (CPU) and suitable memory, such as any suitable type of random access memory (RAM). Program code, comprising software programs and/or data are loaded into the RAM for execution and processing by the CPU. The program code and/or data may be downloaded to the controller in electronic form, over a network, for example. Alternatively or additionally, the program code and/or data may be provided and/or stored on non-transitory tangible media, such as magnetic, optical, or electronic memory. Such program code and/or data, when provided to the processor, produce a machine or special-purpose computer, configured to perform the tasks described herein.

In other embodiments, controller 44 may comprise a general-purpose controller, which is programmed in software to carry out the functions described herein. The software may be downloaded to the controller in electronic form, over a network, for example, or it may, alternatively or additionally, be provided and/or stored on non-transitory tangible media, such as magnetic, optical, or electronic memory.

This particular configuration of system 20 is shown by way of example, in order to illustrate certain problems that are addressed by embodiments of the present invention and to demonstrate the application of these embodiments in enhancing the performance of such a system. Embodiments of the present invention, however, are by no means limited to this specific sort of example system, and the principles described herein may similarly be applied to other sorts of ablation systems used in medical ablation procedures.

Performing Bipolar Ablation Using a Lasso Type Catheter

Figure 2A:
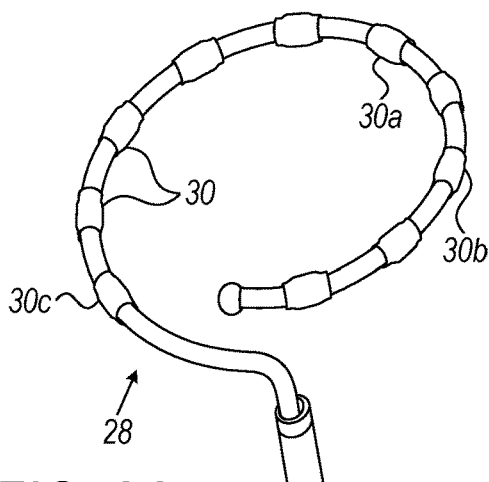
FIGS. 2A and 2B are schematic pictorial illustrations of two shapes of a catheter distal end, in accordance with exemplary embodiments of the present invention.
Figure 2B:
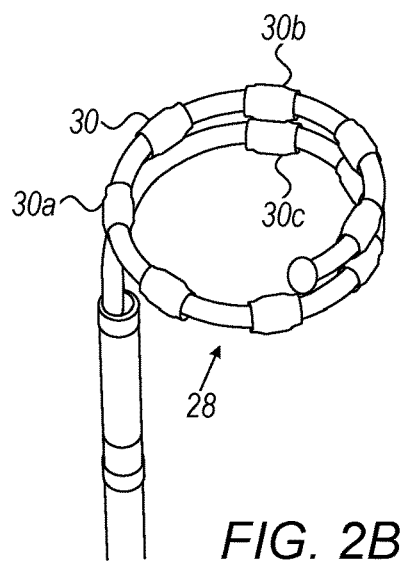

FIGS. 2A and 2B are schematic pictorial illustrations of two shapes of distal end 28 of catheter 26, in accordance with embodiments of the invention. Items similar to those in FIG. 1 are marked with the same labels.

In some embodiments, distal end 28 of catheter 26 comprises a "Lasso" type catheter, having multiple electrodes 30 mounted on a flexible arm, which is configured to conform to the shape of tissue 36 of patient 24. For example, when ablating a pulmonary vein (PV) of heart 34, distal end 28 is configured to conform to the inner diameter of the PV, so as to carry out a PV isolation procedure.

In other embodiments, distal end 28 may comprise any other suitable type of catheter, for example, a multi-arm catheter, such as but not limited to a basket catheter. Note that in both embodiments, electrodes 30 are disposed at distal end 28, using any suitable configuration, e.g., along a longitudinal axis of an arm, or at different arms of the distal end.

Reference is now made to FIG. 2A. In some embodiments, distal end 28 forms a loop, but none of electrodes 30 are positioned in close proximity or making contact with one another.

Reference is now made to FIG. 2B. In some embodiments, distal end 28 is configured to form a tighter loop compared to that of FIG. 2A. In this arrangement, an electrode 30c is placed, in contact with or close proximity to, electrode 30b.

In the example of FIG. 2B, when applying one or more bipolar ablation pulses 40 between electrodes 30a and 30b at least some of the current flowing through electrode 30b may leak (e.g., parasitically) through electrode 30c. As a result of the reduction in power that is actually applied to tissue 36, the bipolar ablation between electrodes 30a and 30b is likely to be inadequate.

Figure 3:
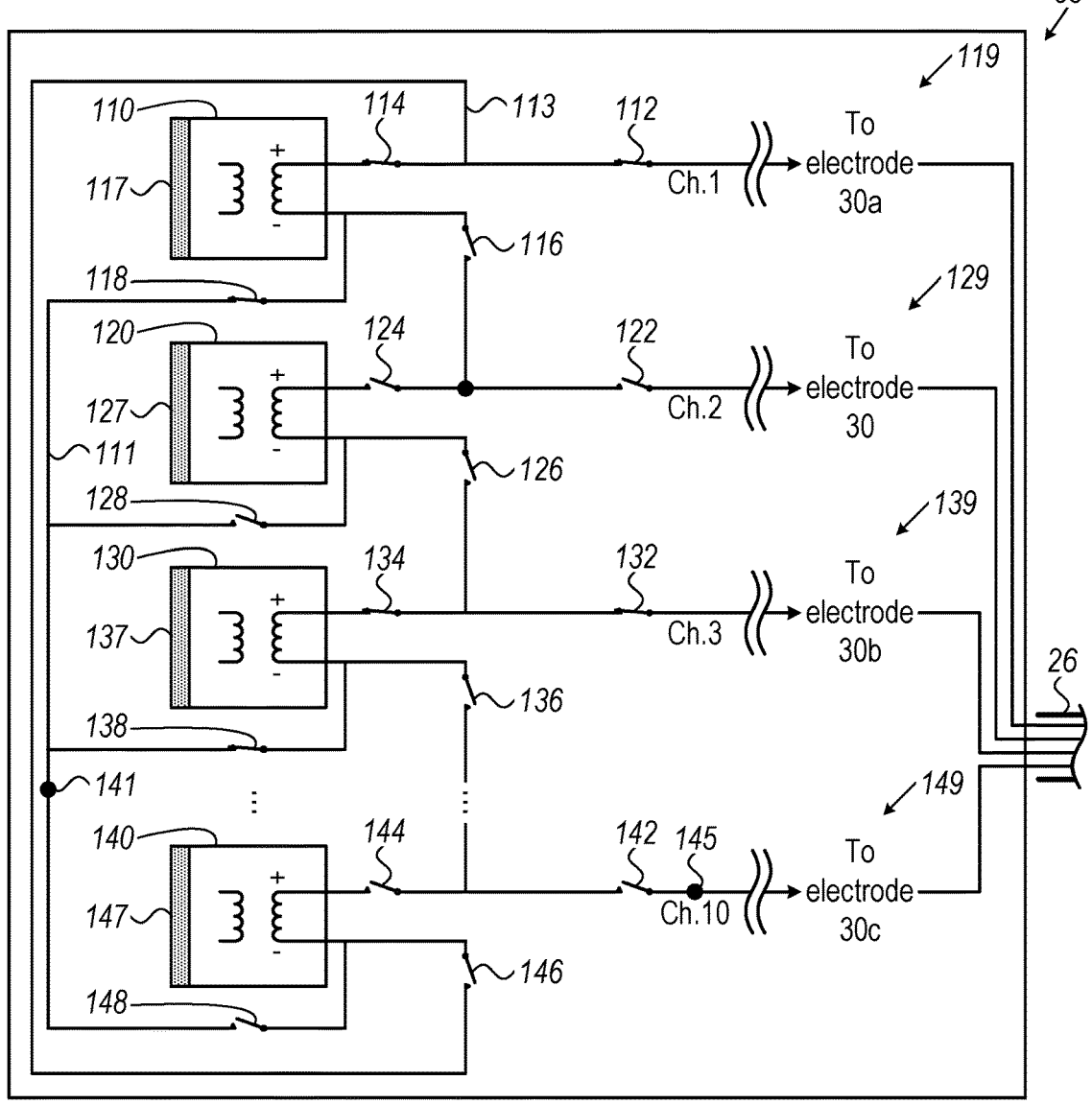
FIG. 3 is a schematic pictorial illustration of a pulse generator for applying ablation signals, in accordance with an exemplary embodiment of the invention.

Estimating Proximity Between Ablation Electrodes by Sensing Voltage on Non-Activated Electrodes FIG. 3 is a schematic pictorial illustration of generator 38, in accordance with an embodiment of the invention. In some embodiments, generator 38 may be integrated in console 56 (as shown in FIG. 1 above), or may be positioned at any other suitable module of system 20.

In some embodiments, generator 38 comprises multiple channels, configured to conduct ablation pulses 40 between pulse generator 38 and respective electrodes 30 of catheter 26, as described in detail herein.

In some embodiments, generator 38 comprises pulse-generation circuits (PGCs) 119, 129, 139 and 149, which are connected to, and are configured to, apply one or more bipolar ablation pulses 40 to electrodes 30a, 30, 30b and 30c, respectively.

In some embodiments, PGC 119 comprises a pulse generating apparatus (PGA) 117 connected to an output transformer, referred to herein as a transformer 110, which is configured to transfer ablation pulses 40 between PGA 117 and electrode 30a of catheter 26. PGC 119 further comprises a channel 1 (shown as "Ch.1" in FIG. 3) made from electrical conductors (e.g., electrical leads or electrical traces) for connecting and disconnecting between PGC 119 and electrode 30a of catheter 26.

In the present example, a first coil of transformer 110 receives one or more of the ablation pulses from PGA 117, and a second coil of transformer 110, which is connected, via channel 1, to a corresponding channel of catheter 26, applies one or more ablation pulses 40 to electrode 30a.

In some embodiments, PGC 119 comprises switches 112 and 114, configured to connect and disconnect between transformer 110 and channel 1, wherein switch 114 is further configured to connect and disconnect between transformer 110 and an electrical trace 113. Note that when switch 114 is closed (as shown in FIG. 3), transformer 110 transfers the one or more ablation pulses to electrode 30a, which is now activated for applying ablation pulses 40 to tissue 36.

In some embodiments, the structure of PGC 119 repeats in the other PGCs of generator 38. For example, PGC 129 comprises: (i) a PGA 127, for producing the ablation pulses as described above for PGA 117, (ii) a channel 2 having the same features of channel 1, and (iii) a transformer 120, which is configured to transfer, via channel 2, ablation pulses 40 between PGA 127 and electrode 30. Similarly, PGC 139 comprises: (i) a PGA 137, for producing the ablation pulses as described above for PGA 117, (ii) a channel 3 having the same features of channel 1, and (iii) a transformer 130, which is configured to transfer, via channel 3, ablation pulses 40 between PGA 137 and electrode 30b.

In some embodiments, PGC 149 comprises: (i) a PGA 147, for producing the ablation pulses as described above for PGA 117, (ii) a channel 4 having the same features of channel 1, and (iii) a transformer 140, which is configured to transfer, via channel 4, ablation pulses 40 between PGA 147 and electrode 30c. Note that in the example of FIG. 3, generator 38 has ten PCGs (wherein only PGCs 119, 129, 139 and 149 are shown) for connecting and disconnecting between each PGA with a respective electrode of catheter 26.

In other embodiments, generator 38 may have any other suitable number of PGCs for connecting and disconnecting between a corresponding number of electrodes of catheter 26. In yet other embodiments, instead of PGAs described above, generator 38 may comprise a single pulse generator (not shown), which is controlled by controller 44 and is configured to supply the ablation pulses to transformers 110, 120, 130 and 140.

In some embodiments, generator comprises a similar routing and switching configuration for each PGC. For example, switches 122 and 124 are configured to connect and disconnect between transformer 120 and channel 2, switches 132 and 134 are configured to connect and disconnect between transformer 130 and channel 3, and switches 142 and 144 are configured to connect and disconnect between transformer 140 and channel 10.

In some embodiments, generator 38 comprises an electrical conductor, referred to herein as a back-patch (BP) 111, which is configured to electrically connect between the transformers of generator 38. BP 111 may serve as a reference for voltage measurement during the application of ablation pulses 40.

In some embodiments, generator 38 further comprises switches 118, 128, 138 and 148 for connecting and disconnecting between BP 111 and transformers 110, 120, 130 and 140, respectively. In the example of FIG. 3, switches 118 and 138 are closed for connecting between BP 111 and transformers 110 and 130, and switches 128 and 148 are opened for disconnecting between BP 111 and transformers 129 and 140, respectively.

In some embodiments, generator 38 further comprises: (i) a switch 116 for connecting and disconnecting between transformers 110 and 120 of neighbor electrodes 30a and 30, (ii) a switch 126 for connecting and disconnecting between transformers 120 and 130 of neighbor electrodes 30 and 30b, (ii) a switch 136 for connecting and disconnecting between transformer 130 and an additional transformer (not shown) of electrode 30b and a neighbor electrode (not shown), and (iv) a switch 146 for connecting and disconnecting between transformers 140 and 110, via trace 113.

In some embodiments, controller 44 is configured to control generator 38 to apply ablation pulses 40: (i) to electrode 30a via transformer 110 and channel 1, and (ii) to electrode 30b via transformer 130 and channel 3. Note that in this operative mode, switches 112, 114 and 118 are closed, so as to apply ablation pulses 40 to electrode 30a, and similarly, switches 132, 134 and 138 are closed, so as to apply ablation pulses 40 to electrode 30b.

In the present example, controller 44 is configured to control generator 38 to apply bipolar ablation pulses 40 having an amplitude of about 900V activated in opposite phase between channels 1 and 3. For example, when channel 1 outputs about +900V to electrode 30a, channel 3 outputs about −900V to electrode 30b. Therefore, the total amplitude of bipolar ablation pulses 40 applied between electrodes 30a and 30b, is about 1800V.

In the context of the present disclosure, the terms "about" or "approximately" for any numerical values or ranges indicate a suitable dimensional tolerance that allows the part or collection of components to function for its intended purpose as described herein.

In some embodiments, during the ablation described above, the voltage amplitude on BP 111, which serves for connecting between transformers 110 and 130, is virtually zero. Similarly, transformers 120 and 140 are idle and the electrodes connected to channels 2 and 4 are not receiving any ablation pulses.

In some embodiments, when applying bipolar ablation pulses 40 between electrodes 30a and 30b, controller 44 is configured to receive a signal. The signal is indicative of a voltage, which is measured between: (i) a point 145 of channel 10 connected to electrode 30c, and (ii) any suitable reference point on BP 111, such as a reference point 141.

In some embodiments, when distal end 28 is arranged as shown in FIG. 2A, electrodes 30, 30a, 30b and 30c are sufficiently far from one another (e.g., about 2 mm or more between any pair of adjacent electrodes). Therefore, when about 1800V is applied between electrodes 30a and 30b (e.g., about +900V voltage is applied to electrode 30a, and at the same time, about −900V is applied to electrode 30b), the voltage measured between points 141 and 145 is about zero.

In some embodiments, when measuring electrical current flowing through activated electrodes, such as electrodes 30a and 30b, the typical impedance measured on each activated electrode is typically constant, e.g., about 100Ω.

In other embodiments, when distal end 28 is arranged as shown in FIG. 2B, electrodes 30b and 30c are in close proximity with one another, e.g., at a distance smaller than about 1 mm, or even in direct contact with one another.

In some embodiments, in the example of FIG. 2B, when about 1800V is applied between electrodes 30a and 30b, the electrical current associated with ablation pulses 40, may flow into electrode 30b. However, due to the close proximity (or physical contact) between electrodes 30b and 30c, voltage has been formed between 30b to electrode 30c. Moreover, when electrodes 30b and 30c are (unintentionally) placed in contact with one another, the surface area of the "combined" electrode (comprising electrodes 30b and 30c) is larger compared to that of electrode 30b. Therefore, the impedance measured on the combined electrode is substantially different than about 100Ω measured in the example described in FIG. 2A above. Moreover, the measured electrical current flowing through the combined electrode substantially differs from the measured electrical current flowing through electrode 30b in the example described in FIG. 2A above.

Additionally or alternatively, the voltage measured between points 141 and 145 is substantially larger than zero. For example, (i) when the distance between electrodes 30b and 30c is about 1 mm, the voltage measured between points 141 and 145 is about 400V, and (ii) when electrodes 30b and 30c are in direct contact the voltage measured between points 141 and 145 is more than about 800V.

In some embodiments, controller 44 is configured to issue a notification in response to detecting that the voltage measured between points 141 and 145, violates a predefined criterion. For example, controller 44 is configured to hold a threshold for the voltage measured between points 141 and 145, and to issue the notification in case the measured voltage exceeds (i.e. is larger than) the threshold voltage. Additionally or alternatively, controller 44 is configured to hold a predefined pulse shape of the voltage measured between points 141 and 145. The pulse shape may have a predefined waveform, e.g., the waveform may comprise the voltage amplitude plotted as a function of the measurement time.

In some embodiments, controller 44 is configured to hold a preassigned threshold of inter-electrode distance (e.g., about 1.5 mm), also referred to herein as a distance threshold. Based on the voltage measured between points 141 and 145, controller 44 is configured to detect whether the distance between electrodes 30b and 30c is smaller than the distance threshold.

In some embodiments, because the measured voltage increases when the distance between electrodes 30b and 30c is reduced, controller 44 is configured, based on the measured voltage, to estimate the distance between electrodes 30b and 30c. For example, when the measured voltage is between about 400V and 550V, the distance between electrodes 30b and 30c is smaller than about 1 mm.

Additionally or alternatively, controller 44 is configured to issue a notification in response to detecting that the current flowing through an active electrode (in the present example, electrode 30b) and/or through a non-active electrode (such as electrode 30c), violates a respective predefined criterion.

In some embodiments, in order to measure of the signal indicative of the voltage between points 141 and 145, controller 44 is configured to disconnect electrode 30c from transformer 140. For example, by having switches 142 and 144 opened.

Figure 4:
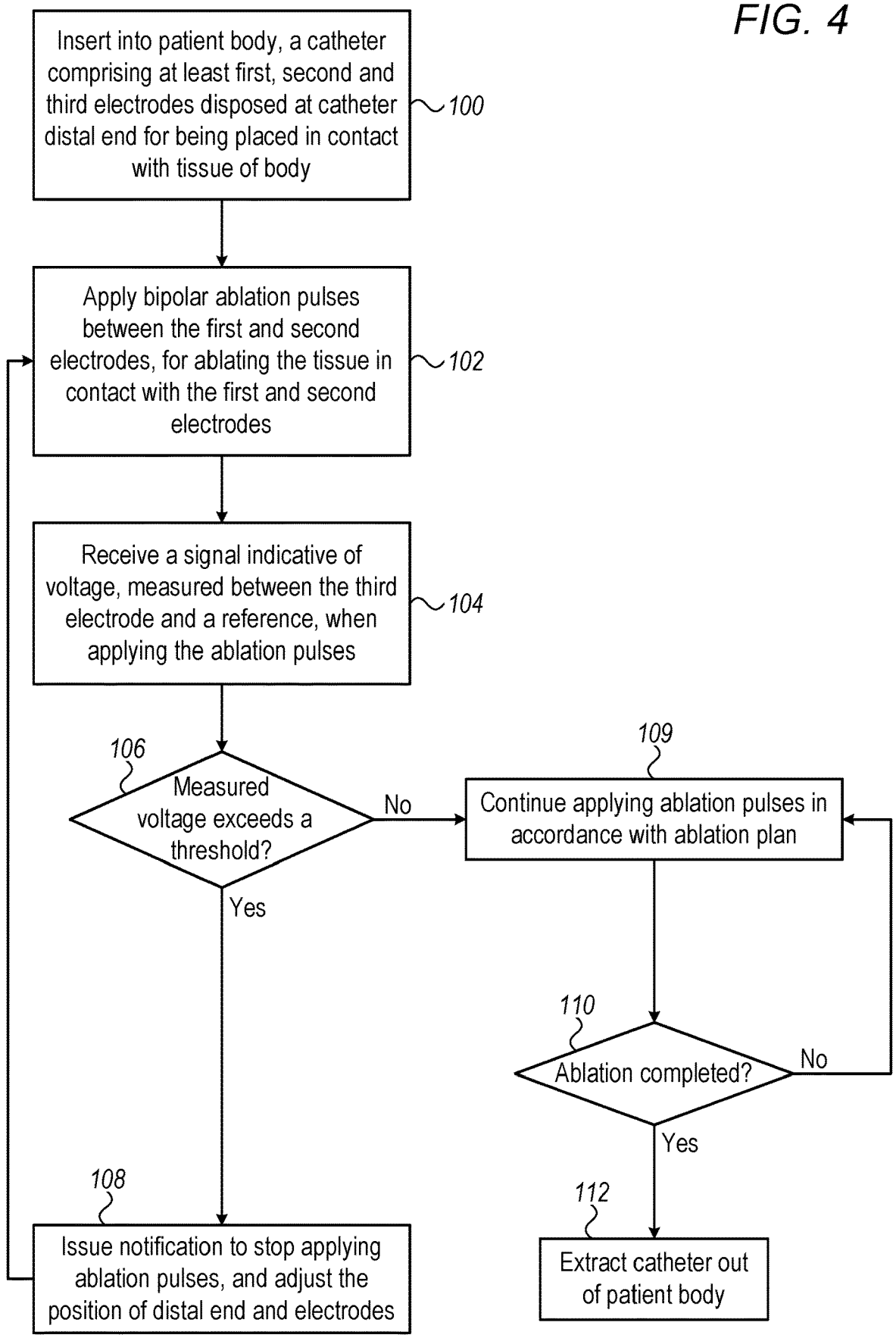
FIG. 4 is a flow chart that schematically illustrates a method for detecting contact and proximity between ablation electrodes during a bipolar ablation procedure, in accordance with an exemplary embodiment of the present invention.

FIG. 4 is a flow chart that schematically illustrates a method for detecting contact and proximity between ablation electrodes 30b and 30c during a bipolar ablation procedure, in accordance with an embodiment of the present invention.

The method begins with a catheter insertion step 100, with the insertion of catheter 26 into heart 34 or any other suitable organ in the body of patient 24. As described in FIGS. 1-3 above, catheter 26 comprises at least electrodes 30a, 30b and 30c, disposed at distal end 28 for being placed in contact with tissue 36 of heart 34.

At a tissue ablating step 102, controller 44 controls generator 38 to apply one or more bipolar ablation pulses 40 between electrodes 30a and 30b, for ablating tissue 36, which is in contact with electrodes 30a and 30b, as described in FIGS. 1, 2A and 2B above.

At a signal receiving step 104, when applying ablation pulses 40, controller 44 receives a signal indicative of the voltage measured between points 141 and 145, which constitutes the voltage between electrode 30c and BP 111 that serves as a reference, as described in FIG. 3 above.

At a first decision step 106, controller 44, which holds one or more thresholds of electrical parameters, such as voltage threshold, checks whether the measured parameter exceeds the respective threshold. Additionally or alternatively, controller 44 may hold a distance threshold, and estimates the distance between electrodes 30b and 30c, based on the measured voltage. In some embodiments, controller 44 checks whether the estimated distance is smaller or larger than the distance threshold.

In some embodiments, in step 106 controller 44 may detect that the voltage measured between points 141 and 145 is larger than the voltage threshold, and/or the estimated distance is smaller than the distance threshold. In such embodiments, the method proceeds to an alerting and adjusting step 108, with issue notification by controller 44 to stop applying bipolar ablation pulses 40. Additionally or alternatively, controller 44 may automatically control generator 38 to stop applying bipolar ablation pulses 40 between electrodes 30a and 30b.

In some embodiments, controller 44 may also issue a notification to physician 22 to adjust the position of the electrodes of distal end 28 relative to tissue 36, because an active electrode (e.g., electrode 30b) and a non-active electrode (e.g., electrode 30c) are in contact with one another or positioned in too close proximity to one another.

In some embodiments, after adjusting the position of the electrodes of distal end 28 relative to tissue 36, controller 44 may estimate the need to apply additional bipolar ablation pulses 40 to tissue 36, and in case more ablation is needed, the method loops back to step 102 for applying the ablation pulses as described above.

In other embodiments, in step 106 controller 44 may detect that the voltage measured between points 141 and 145 is smaller than the voltage threshold, and/or the estimated distance is larger than the distance threshold. In such embodiments, the method proceeds to an ablation continuation step 109, and controller 44 controls generator 38 to continue applying one or more bipolar ablation pulses 40 between electrodes 30a and 30b, in accordance with ablation plan.

At a second decision step 110, controller 44 checks whether the ablation procedure has been completed, e.g., in case sufficient bipolar ablation pulses 40 have been applied to tissue 36. In case the ablation procedure has not been completed, the method loops back to step 109. In case the ablation has been completed, the method proceeds to a catheter extraction step 112, which concludes the method, so that physician 22 extracts catheter 26 out of the body of patient 24.

Although the embodiments described herein mainly address bipolar ablation procedures using a flexible catheter, e.g., lasso type, having multiple electrodes, the methods and systems described herein can also be used in other applications, such as in bipolar ablation procedures using other sorts of catheters, for maintaining predefined distance between electrodes of such catheters. Moreover, the embodiments described herein may be also used in various types of electroporation procedures, such as but not limited to irreversible electroporation, and in electrosurgical procedures.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system for detecting contact and proximity between ablation electrodes by sensing changes in voltage morphology of non-activated electrodes, the system comprising:
a pulse generator, which is configured to apply one or more bipolar ablation pulses between a first and second electrode of a catheter that are contacting tissue within a body, for ablating the tissue in contact with the first and second electrodes, wherein the catheter additionally includes a third electrode on which the pulse generator does not apply an ablation pulse; and
a controller, which is configured to: (i) control the pulse generator to apply the one or more bipolar ablation pulses between the first and second electrodes, (ii) monitor voltage between the third electrode and a reference during application of the one or more ablation pulses, wherein the third electrode is a non-active electrode, (iii) compare the voltage to a reference voltage stored in memory associated with the controller, and (iv) issue a notification during application of the one or more ablation pulses in response to detecting that the voltage violates a predefined criterion based on the comparing.

2. The system according to claim 1, wherein, in detecting that the voltage violates the predefined criterion, the controller is configured to detect that a distance between (i) at least one of the first and second electrodes, and (ii) the third electrode, is smaller than a distance threshold.

3. The system according to claim 1, wherein the pulse generator comprises first, second and third pulse-generation circuits having respective output transformers, which are selectively connected to the first, second and third electrodes, respectively, and are configured to selectively apply the bipolar ablation pulses between pairs of the first, second and third electrodes.

4. The system according to claim 3, wherein, the third electrode is selectively disconnected from the third output transformer over a duration of monitoring the voltage between the third electrode and the reference.

5. The system of claim 1; wherein in detecting that the voltage violates the predefined criterion, the controller is configured to compare a waveform of the voltage monitored to a waveform of the reference voltage.

6. The system of claim 1, wherein detecting that the voltage violates the predefined criterion includes detecting that the voltage monitored exceeds a voltage threshold defined based on the reference voltage signal.

7. A method for detecting contact and proximity between ablation electrodes by sensing changes in voltage morphology of non-activated electrodes, the method comprising:
applying one or more bipolar ablation pulses between a first electrode and a second electrode of a catheter that are contacting tissue within a body, for ablating the tissue in contact with the first and second electrodes, wherein the catheter additionally includes a third electrode on which the pulse generator does not apply an ablation pulse;
monitor voltage between the third electrode and a reference during application of the one or more ablation pulses, wherein the third electrode is a non-active electrode;
comparing the voltage to a reference voltage stored in memory, and
issuing a notification during application of the one or more ablation pulses in response to detecting that the voltage violates a predefined criterion based on the comparing.

8. The method according to claim 7, wherein detecting that the voltage violates the predefined criterion, comprises detecting that a distance between: (i) at least one of the first and second electrodes, and (ii) the third electrode, is smaller than a distance threshold.

9. The method according to claim 7, wherein applying one or more bipolar ablation pulses comprises, in a pulse generator comprising first, second and third pulse-generation circuits having respective output transformers, which are selectively connected to the first, second and third electrodes, respectively, selectively applying the bipolar ablation pulses between pairs of the first, second and third electrodes.

10. The method according to claim 9, wherein the third electrode is selectively disconnected from the third output transformer over a duration of monitoring the voltage between the third electrode and the reference.

11. The method of claim 7; wherein in detecting that the voltage violates the predefined criterion, the controller is configured to compare a waveform of the voltage monitored to a waveform of the reference voltage.

12. The method of claim 7, wherein detecting that the voltage violates the predefined criterion includes detecting that the voltage monitored exceeds a voltage threshold defined based on the reference voltage signal.

* * * * *